United States Patent [19]

Biendarra et al.

[11] Patent Number: 5,616,158

[45] Date of Patent: Apr. 1, 1997

[54] MOISTURE ABSORBING MEDIA FILTER

[75] Inventors: Bruce S. Biendarra, West Bend; Robert H. Ricciardelli, Waukesha, both of Wis.

[73] Assignee: Pryon Corporation, Menomonee Falls, Wis.

[21] Appl. No.: 440,943

[22] Filed: May 15, 1995

[51] Int. Cl.$^6$ .................................................. B01D 35/143
[52] U.S. Cl. ......................... 55/275; 55/DIG. 34; 96/118; 128/205.27
[58] Field of Search .............................. 55/275, 274, 270, 55/DIG. 34; 128/205.12, 205.27; 96/118–120

[56] References Cited

U.S. PATENT DOCUMENTS

| | | | |
|---|---|---|---|
| 2,528,539 | 11/1950 | Norgren et al. | 55/275 |
| 3,306,011 | 2/1967 | Dvorkin | 55/275 X |
| 3,505,783 | 4/1970 | Graham | 55/275 X |
| 3,705,480 | 12/1972 | Wireman | 55/275 X |
| 4,197,858 | 4/1980 | Osborn | 128/718 |
| 4,278,453 | 7/1981 | Klein | 55/275 X |
| 4,304,578 | 12/1991 | Hakala et al. | 55/439 |
| 4,350,508 | 9/1982 | Santoro et al. | 55/275 X |
| 4,446,869 | 5/1984 | Knodle | 128/716 |
| 4,530,706 | 7/1985 | Jones | 55/DIG. 34 |
| 4,579,568 | 4/1986 | Ricciardelli et al. | 128/719 X |
| 4,713,095 | 12/1987 | Ricciardelli | 55/270 X |
| 4,717,403 | 1/1988 | Choksi | 55/429 |
| 4,827,778 | 5/1989 | Bossart et al. | 73/863.21 |
| 4,924,860 | 5/1990 | Larsen et al. | 128/205.12 |
| 4,985,055 | 1/1991 | Thorne et al. | 55/270 X |
| 5,131,387 | 7/1992 | French et al. | 128/205.27 |
| 5,209,761 | 5/1993 | Ivester et al. | 55/213 X |
| 5,368,021 | 11/1994 | Beard et al. | 128/205.12 |
| 5,482,541 | 1/1996 | Maier-Laxhuber et al. | 55/274 X |

FOREIGN PATENT DOCUMENTS

644230  7/1962  Canada .................................. 55/275

*Primary Examiner*—Richard L. Chiesa
*Attorney, Agent, or Firm*—Donald J. Ersler

[57] ABSTRACT

A moisture absorbing media filter includes a housing into which a moisture absorbing material is placed, an end cap fabricated from a clear plastic fits over the housing, exhalations pass through the end cap into an impermeable tube which terminates at substantially the middle of a bore contained in the moisture absorbing material. A tapered chamber follows the impermeable tube and terminates at the end of the moisture absorbing material, a reduced passage follows a pellet filter and leads to an outlet opening, a dyeing agent is deposited into the tapered chamber, a predetermined amount of low vapor pressure, water soluble liquid is also deposited into the tapered chamber. Exhalations enter the inlet opening and pass through the impermeable tube into the tapered chamber, low vapor pressure, water soluble liquid deposited in the tapered chamber allows moisture in the gas to be absorbed by the moisture absorbing material but not the gas itself. Moisture absorbed by the filter forces the dyeing agent outward to the cylindrical body of the housing and to the end cap thus indicating that the filter should be discarded. Gas passes through a pellet filter which will not allow the gas to pass if the pellet filter has become substantially saturated with moisture. The gas then passes into a moisture filter which contains a second pellet filter which operates as the first pellet filter and finally, the gas passes into a monitoring system.

21 Claims, 5 Drawing Sheets

MOISTURE ABSORBING MEDIA FILTER

BACKGROUND OF THE INVENTION

1. Field of the Invention

The present invention relates generally to systems for monitoring a medical patient's exhalation and more specifically to a media filter which separates the moisture from the gases of the exhalation in anticipation of gas analysis or measurement.

2. Discussion of the Prior Art

In the course of medical treatment, it is often desirable to monitor a patient's exhalation and sometimes measure and analyze the gases. Analysis of the gases require that the exhalation be free from moisture which is contained in the exhalation. The removal of moisture is accomplished by a moisture filter.

There are two types of moisture filters on the market today, the first being a chamber type and the second being a media type. Simply stated, the chamber type has an inlet, an outlet and a chamber. The gases pass through the inlet, moisture collects in the chamber and the moisture free gases pass through the outlet into a monitoring system for analysis. The media type has an inlet, an outlet and a filtering material. The gases pass through the inlet into a filtering material, the filtering material traps or retains the moisture from the gases and the moisture free gases pass through the outlet into a monitoring system for analysis. The present invention is a media type moisture filter. The following descriptions are two media type moisture filters that have been disclosed in recent years.

In U.S. Pat. No. 4,446,869, Knodle discloses a media type filter in which a patient's exhalations pass through a cylindrical chamber in a moisture absorbing material. Moisture in the gases is absorbed by the moisture absorbing material. A pellet filter at the outlet of the moisture absorbing material prevents passage of gases through the outlet by swelling with moisture if the moisture absorbing material becomes substantially saturated with moisture.

In U.S. Pat. No. 5,131,387, French et al. discloses a media type filter in which a patient's exhalations pass through a hydrophilic material contained in a housing. A side passage in the housing allows a moisture absorbing material to wick off moisture contained in the hydrophilic material. A pellet filter at the outlet of the hydrophilic material prevents passage of the gases if the moisture absorbing material becomes substantially saturated with moisture. The pellet filter, being of a microporous hydrophobic material will not allow passage of condensed moisture.

Both these filters have common shortcomings. First, there is no indication given when the filter becomes saturated with moisture. When saturation of the filter occurs, an alarm will sound requiring possible emergency response from the caregiver. Second, some of the exhalation gases will be absorbed by the moisture absorbing material in addition to moisture which renders a less accurate reading of the gases present in the patient's exhalation.

Accordingly, there is a clearly felt need in the art for a media filter which gives an indication when the filter is becoming substantially saturated with moisture. There is also a need for an improvement to the moisture absorbing material which more thoroughly blocks the moisture absorbing material from absorbing gases of the patient's exhalation. There is also a need for a media filter which is simpler and has fewer parts than the prior art. These unresolved problems are clearly felt in the art and are solved by the disclosed invention in the manner described below.

SUMMARY OF THE INVENTION

The primary objective of the present invention is to provide a media filter which absorbs moisture from a patient's exhalations while giving an indication to a caregiver that the moisture absorbing material is becoming substantially saturated. The present invention also prevents less gas from the patient's exhalations from being absorbed into the moisture absorbing material than the prior art.

According to the present invention, a moisture absorbing media filter includes a housing into which a moisture absorbing material fits. An end cap, constructed from clear plastic fits over the housing, the end cap has an inlet opening through which exhalations pass. An impermeable tube is inserted into a bore contained in the end cap, the tube passes through a bore contained in the moisture absorbing material and terminates at substantially the middle of the bore in the moisture absorbing material. A tapered chamber follows the impermeable tube and terminates at the end of a moisture absorbing material. A space separates the moisture absorbing material from a pellet filter. A reduced passage follows the pellet filter and leads to an outlet opening. A dyeing agent is deposited into the tapered chamber. A predetermined amount of a low vapor pressure, water soluble liquid is also deposited into the tapered chamber. Exhalations enter the inlet opening and pass through the impermeable tube into the tapered chamber.

The low vapor pressure, water soluble liquid is deposited in the tapered chamber allows moisture in the gas to be absorbed by the moisture absorbing material but not the gas itself. Moisture absorbed by the moisture absorbing material forces the dyeing agent outward to the cylindrical body of the housing and to the end cap, thus indicating when the media filter is substantially saturated with moisture and should be discarded. Gas passes through a pellet filter which will not allow the gas to pass through thereof if the pellet filter swells with moisture. If the pellet filter does not swell, the gas then passes through a moisture filter which contains a second pellet filter which operates as the first pellet filter, and finally, the gas passes into a monitoring system.

Accordingly, it is an object of the present invention to provide a moisture absorbing media filter which indicates when the moisture absorbing material is becoming saturated with moisture.

It is a further object of the present invention to provide a moisture absorbing media filter which has a moisture absorbing material which absorbs less gas from the exhalation while satisfactorily absorbing moisture.

It is yet another object of the present invention to provide a moisture absorbing media filter which has fewer parts than that of the prior art.

These and additional objects, advantages, features and benefits of the present invention will become apparent from the following specification.

DETAILED DESCRIPTION OF THE PREFERRED EMBODIMENT

Figure 1:
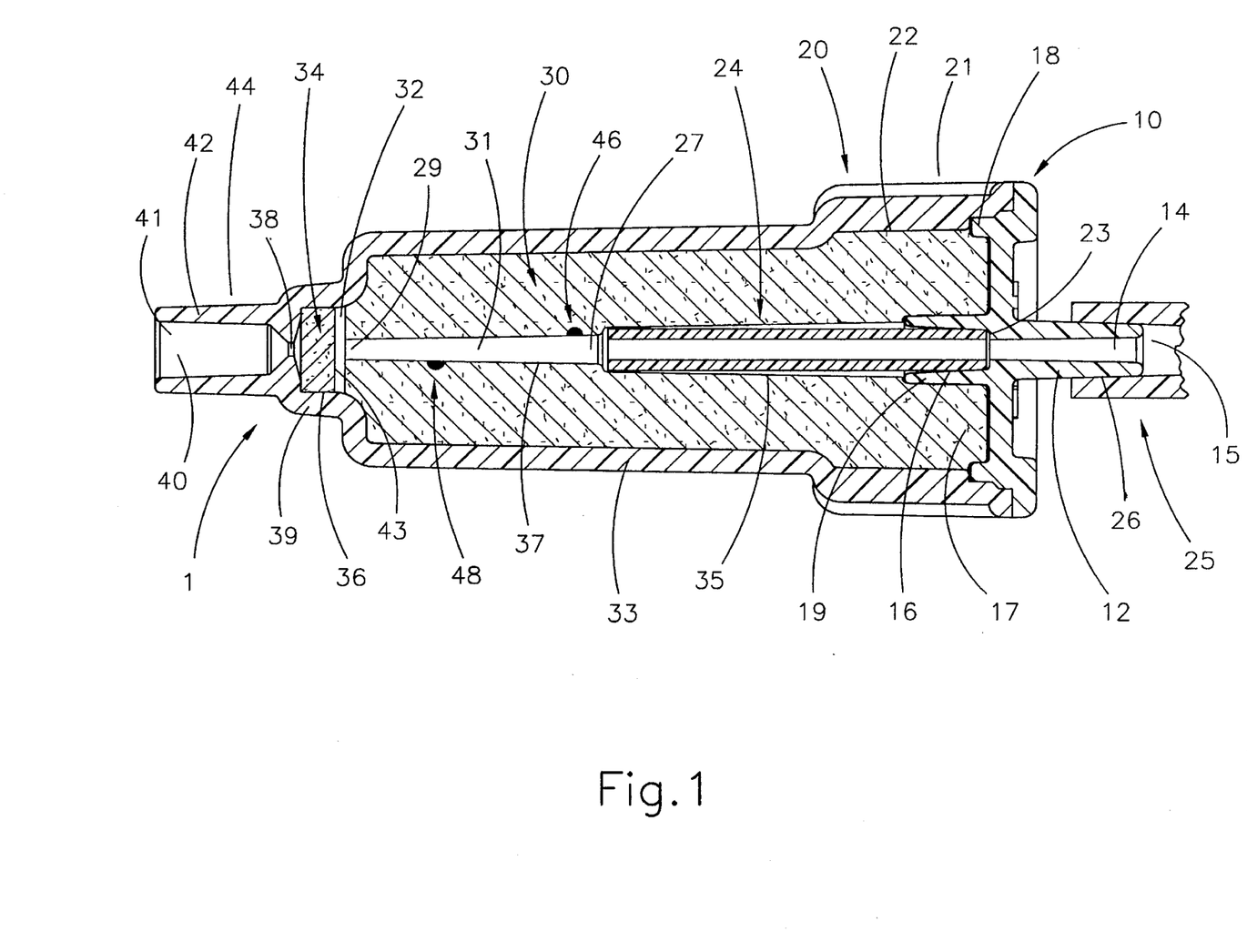
FIG. 1 is a cross sectional detail view of a moisture absorbing media filter in accordance with the present invention.

With reference now to the drawings, and particularly to FIG. 1, there is shown a cross sectional detail view of a moisture absorbing media filter 1 in accordance with the present invention. The moisture absorbing media filter 1 comprises an end cap 10, a housing 20, an impermeable tube 24, a moisture absorbing material 30 and a pellet filter 34.

The end cap 10 has an inlet nozzle 12 protruding from a first end 15 and a boss 19 protruding from a second end 17. A nozzle profile 26 of the inlet nozzle 12 is shaped to allow a medical tube 25 to fit over the inlet nozzle 12. Material is removed from the boss 19 to form a bore 16 which is sized to snugly fit the impermeable tube 24 such that no leakage of gas occurs from the bore 16 into the moisture absorbing material 30. It is possible to eliminate the impermeable tube 24 from the moisture absorbing media filter 1 and still have normal operation thereof. The purpose of the impermeable tube 24 is to utilize the full capacity of the moisture absorbing media 30 by forcing moisture absorbed by the moisture absorbing media 30 to start propagation from a further distance from the end cap 10.

An inlet opening 14 passes through the end cap 10 and terminates at a bottom 23 of the bore 16. A ring 18 protrudes from the second end 17 of the end cap 10, the ring 18 is sized to fit a bore 22 in the housing 20. At assembly, the ring 18 of the end cap 10 is ultrasonically welded to the bore 22 of the housing 20 such that no leakage of moisture from the moisture absorbing material 30 occurs. The end cap 10 is fabricated from clear plastic material such that a dyeing agent 46 may be viewed when the moisture absorbing material 30 becomes substantially saturated with moisture.

The housing 20 has a cylindrical body 33, a first end 21 and a second end 44. An outlet nozzle 42 protrudes from the second end 44 of the housing 20. The outlet nozzle 42 has a first end 39 and a second end 41. An outlet opening 40 passes through the second end 41 of the outlet nozzle 42 and terminates at substantially the middle of the outlet nozzle 42. Material is removed to form a bore 36 which is sized to receive the pellet filter 34 in the first end 39 of the outlet nozzle 42. Gas flows through the pellet filter 34, the reduced passage 38 and out of the housing 20 through the outlet opening 40. The housing 20 is fabricated from clear plastic material such that the dyeing agent 46 may be viewed when the moisture absorbing material 30 becomes substantially saturated with moisture.

The moisture absorbing material 30 is sized to fit inside the cylindrical body 33 of the housing 20. A bore 35 passes through the moisture absorbing material 30 and terminates substantially in the middle thereof. A tapered chamber 31 extends from the bore 35 and passes through the remaining length of the moisture absorbing material 30. The tapered chamber 31 is shaped such that more moisture is absorbed at the entrance 27 of said tapered chamber by the moisture absorbing material than at the exit 29 thereof. The moisture absorbing material 30 has a porosity of approximately 30 microns.

A space 32 occurs between the pellet filter 34 and the moisture absorbing material 30 at second end 44 of the housing 20. The pellet filter 34 has a frontal surface area 43. The space 32 exists to allow the frontal surface area 43 of the pellet filter 34 to be penetrated by advancing gas flow. The pellet filter 34 has a porosity of approximately 90 microns. If the pellet filter 34 becomes saturated with moisture, the pellet filter 34 will not allow gas to flow to the outlet opening 40 of the outlet nozzle 42.

A dyeing agent 46 in a predetermined amount is deposited in the tapered chamber 31 of the moisture absorbing material 30. Moisture absorbed by the moisture absorbing material 30 forces the dyeing agent 46 outward to the cylindrical body 33 of the housing 20 and to the end cap 10 when the moisture absorbing material 30 is substantially saturated with moisture. When moisture absorbing material 30 completely takes on the color of the dyeing agent 46 as visually observed through the end cap 10, the moisture absorbing media filter 1 should be discarded.

A predetermined amount of a low vapor pressure, water soluble liquid 48 is deposited in the tapered chamber 31 of the moisture absorbing material 30. The low vapor pressure, water soluble liquid 48 will be absorbed by the moisture absorbing material 30. The low vapor pressure, water soluble liquid 48 is readily dissolved in water and allows moisture to be absorbed by the moisture absorbing material 30 while making it more difficult for gases to be absorbed by the moisture absorbing material 30 than if the moisture absorbing material 30 was not treated with the low vapor pressure, water soluble liquid 48. An example of a low pressure, water soluble liquid that has been successfully used in this application is glycerol.

An illustration of the operation of the moisture absorbing media filter 1 follows. An exhalation enters the inlet opening 14 and passes through the impermeable tube 24. When the exhalation enters the tapered chamber 31, moisture is absorbed by the moisture absorbing material 30. The gas portion of the exhalation passes through the pellet filter 34, the reduced opening 38 and the outlet opening 41.

Figure 2:
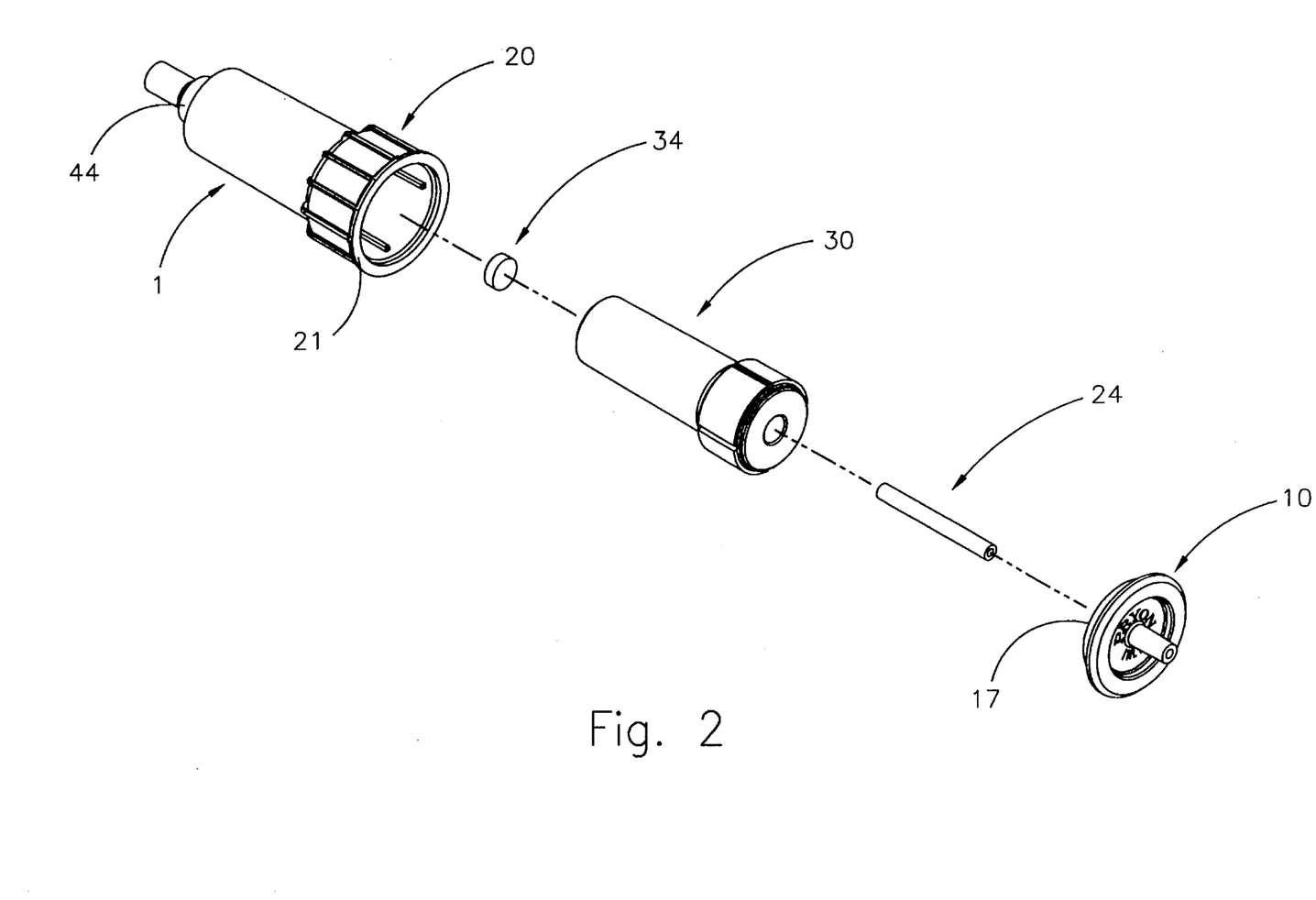
FIG. 2 is a perspective exploded detail view of the moisture absorbing media filter in accordance with the present invention.

FIG. 2 shows an exploded perspective view of the moisture absorbing media filter 1. With reference to FIGS. 1 and 2, the pellet filter 34 fits inside the housing 20 at second end thereof. The moisture absorbing material 30 also fits into the housing 20. The impermeable tube 24 snugly fits into the end cap 10 at the second end 17 thereof. The second end 17 of the end cap 10 snugly fits into the first end 21 of the housing 20.

Figure 3:
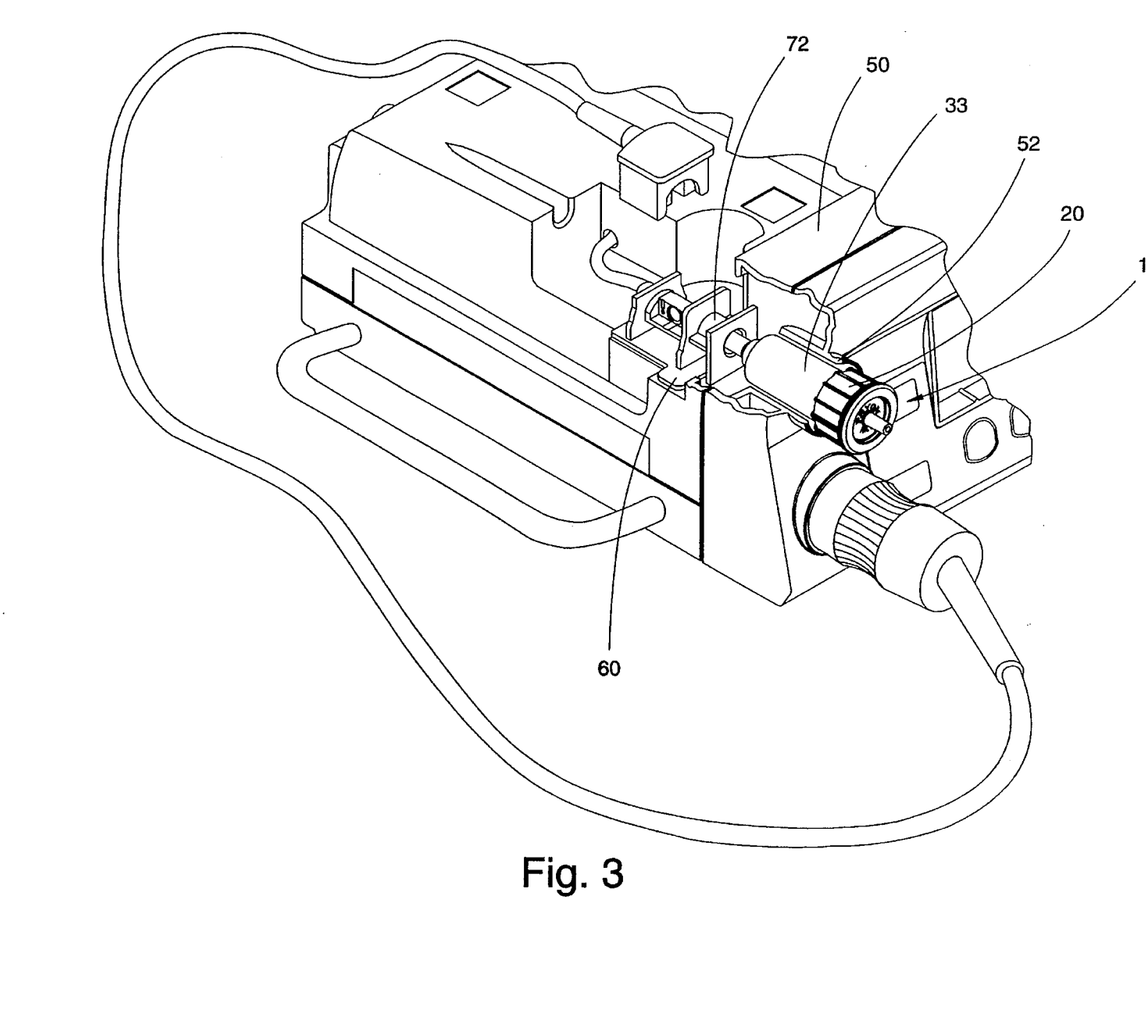
FIG. 3 is a perspective view of a monitoring system with the moisture absorbing media filter installed in accordance with the present invention.

FIG. 3 shows a perspective view of a monitoring system 50 with the moisture absorbing media filter 1 installed. A nozzle profile 54 of the outlet nozzle 42 is shaped to be received by the inlet nozzle 72 of moisture filter 60. An opening 52 in the monitoring system 50 receives the cylindrical body 33 of housing 20.

Figure 4:
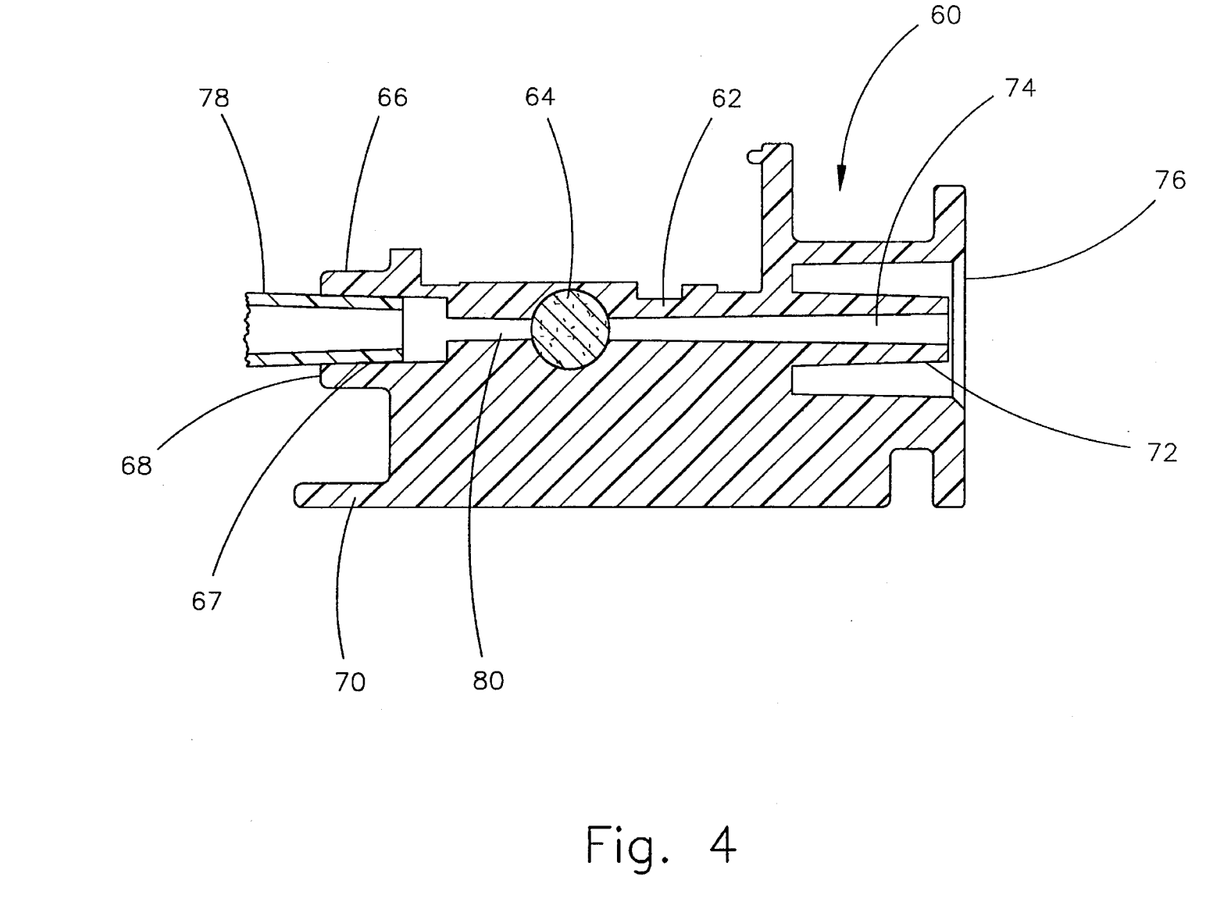
FIG. 4 is a cross sectional detail view of a moisture filter in accordance with the present invention.

FIG. 4 shows a cross sectional detail view of a moisture filter 60 in accordance with the present invention. The moisture filter 60 comprises a housing 62, an inlet nozzle 72, a pellet filter 64, and an outlet nozzle 66.

The housing 62 has a first end 76, a second end 68 and a base 70, the housing 62 is fabricated of a molded plastic. The inlet nozzle 72 is molded as an integral part of the housing 62 at the first end 76. The housing 62 is molded around the pellet filter 64 and the pellet filter 64 is disposed in substantially the middle of housing 62. The pellet filter 64 has a porosity of approximately 90 microns. An inlet opening 74 extends through the inlet nozzle 72 and communicates with the pellet filter 64. The outlet nozzle 66 is molded as an integral part of the housing 62 at the second end 68. A tube clearance 67 extends through the outlet nozzle 66 and communicates with an outlet opening 80 which extends through housing 62 and communicates with the pellet filter 64. The tube clearance 67 is sized to receive a transfer tube 78.

An illustration of the operation of the moisture filter 60 follows. Gas enters the inlet opening 74, travels through the pellet filter 64 and finally through the outlet nozzle 66. If the pellet filter 64 becomes saturated with moisture, the pellet filter 64 will not allow gas flow through the outlet nozzle 66.

Figure 5:
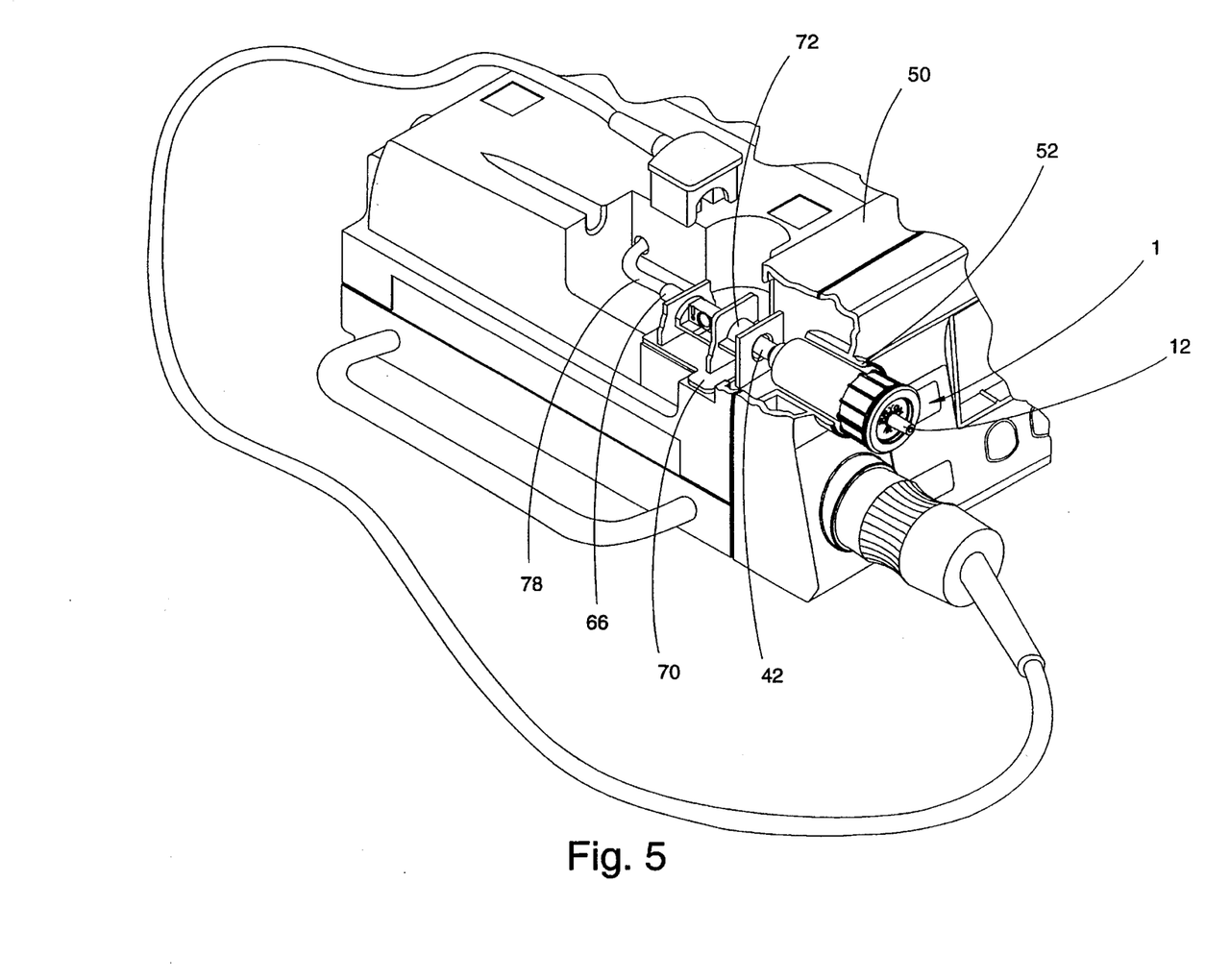
FIG. 5 is a perspective view of the monitoring system with the moisture filter and moisture absorbing media filter installed in accordance with the present invention.

FIG. 5 is a perspective view of the monitoring system 50 with the moisture filter 60 and the moisture absorbing media filter 1 installed. The base 70 of the moisture filter 60 fits into the monitoring system 50, the outlet nozzle 42 of the moisture absorbing media filter 1 fits into the inlet nozzle 72 of the moisture filter 60. The transfer tube 78 fits into outlet nozzle 66. Gas enters the inlet nozzle 12, passes through the moisture absorbing media filter 1 and the moisture filter 60 into the transfer tube 78 and finally, into the monitoring system 50.

While a particular embodiment of the invention has been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A moisture absorbing media filter comprising:

a pellet filter a housing having a first end and a second end;

an outlet nozzle protruding from said second end of said housing, said housing having an opening at said second end which is sized to receive said pellet filter;

a moisture absorbing material which is inserted inside said housing, said moisture absorbing material having an opening through the length thereof;

an end cap having a first end and a second end, said end cap having an inlet nozzle protruding from said first end thereof, said second end of said end cap being structured to seal said first end of said housing;

a dyeing agent applied to said opening in said moisture absorbing material; and a predetermined amount of low vapor pressure, water soluble liquid, said low vapor pressure, water soluble liquid being applied to said opening in said moisture absorbing material.

2. The moisture absorbing media filter of claim 1, wherein:

said opening of said moisture absorbing material becomes a tapered chamber at substantially the middle of said moisture absorbing material; and said tapered chamber having an entrance and an exit, said tapered chamber being structured to absorb more moisture at said entrance than at said exit.

3. The moisture absorbing media filter of claim 2, wherein:

said pellet filter being separated from said moisture absorbing material by a space, said space exposing a frontal surface area of said pellet filter to the flow of gas from said tapered chamber of said moisture absorbing material, said pellet filter preventing the flow of moisture and gas when becoming substantially saturated with moisture.

4. The moisture absorbing media filter of claim 1 further comprising:

an impermeable tube;

said end cap having a bore located at said second end thereof, said bore of said end cap communicating with said inlet nozzle of said end cap;

said impermeable tube being received by said bore of said end cap;

said end cap having a ring disposed at said second end, said ring of said end cap being ultrasonically welded to said bore of said housing; and wherein no leakage of moisture flows past the union of said ring of said end cap and said bore of said housing, said impermeable tube fits snugly inside said bore of said end cap, wherein no gas leakage flows past the union of said impermeable tube and said bore of said end cap.

5. The moisture absorbing media filter of claim 1, wherein said housing being fabricated from clear plastic to enable viewing propagation of said dyeing agent in said moisture absorbing material.

6. The moisture absorbing media filter of claim 1, wherein:

said dyeing agent having a color;

said housing being fabricated from a clear plastic, said moisture absorbing material being viewable through said clear plastic of said housing;

said end cap being fabricated from a clear plastic, said moisture absorbing material being viewable through said clear plastic of said end cap; and said dyeing agent being applied to said moisture absorbing material, wherein said dyeing agent being forced outward through said moisture absorbing material by absorbed moisture until said dyeing agent is viewable through said housing and said end cap, said color of said dyeing agent indicating that said moisture absorbing filter is substantially saturated with moisture.

7. The moisture absorbing media filter of claim 1, wherein:

said predetermined amount of low vapor pressure, water soluble liquid being applied to said opening of said moisture absorbing filter, wherein said predetermined amount of low vapor pressure, water soluble liquid decreasing the amount of gases absorbed by said moisture absorbing material while still absorbing a sufficient amount of moisture.

8. A moisture absorbing media filter comprising:

a pellet filter;

a housing having a first end and a second end;

an outlet nozzle protruding from said second end of said housing, said housing having an opening at said second end which is sized to receive said pellet filter;

a moisture absorbing material which is inserted inside said housing, said moisture absorbing material having an opening through the length thereof;

an end cap having a first end and a second end, said end cap having an inlet nozzle protruding from said first end thereof, said second end of said end cap being structured to seal said first end of said housing; and a predetermined amount of low vapor pressure, water soluble liquid, said low vapor pressure, water soluble liquid being applied to said opening in said moisture absorbing material, wherein said predetermined amount of low vapor pressure, water soluble liquid decreasing the amount of gases absorbed by said moisture absorbing material while still absorbing a sufficient amount of moisture.

9. The moisture absorbing media filter of claim 8, wherein:

said opening of said moisture absorbing material becomes a tapered chamber at substantially the middle of said moisture absorbing material; and said tapered chamber having an entrance and an exit, said tapered chamber being structured to absorb more moisture at said entrance than at said exit.

10. The moisture absorbing media filter of claim 9, wherein:

said pellet filter being separated from said moisture absorbing material by a space, said space exposing a frontal surface area of said pellet filter to the flow of gas from said tapered chamber of said moisture absorbing material, said pellet filter preventing the flow of moisture and gas when becoming substantially saturated with moisture.

11. The moisture absorbing media filter of claim 8, further comprising:

an impermeable tube;

said end cap having a bore located at said second end thereof, said bore of said end cap communicating with said inlet nozzle of said end cap;

said impermeable tube being received by said bore of said end cap;

said end cap having a ring disposed at said second end thereof, said ring of said end cap being ultrasonically welded to said first end of said housing; and wherein no leakage of moisture flows past the union of said ring of said end cap and said first end of said housing, said impermeable tube fits snugly inside said bore of said end cap, wherein no gas leakage flows past the union of said impermeable tube and said bore of said end cap.

12. The moisture absorbing media filter of claim 8, wherein:

said predetermined amount of low vapor pressure, water soluble liquid being applied to said opening of said moisture absorbing filter, wherein said predetermined amount of low vapor pressure, water soluble liquid decreasing the amount of gases absorbed by said moisture absorbing material while still absorbing a sufficient amount of moisture.

13. A moisture absorbing media filter system comprising:

a moisture absorbing media filter, and a moisture filter;

said moisture absorbing media filter comprising:

a first housing having a first end and a second end;

an outlet nozzle protruding from said second end of said first housing, said first housing having an opening at said second end which is sized to receive a pellet filter;

a moisture absorbing material which is inserted inside said first housing, said moisture absorbing material having an opening through the length thereof;

an end cap having a first end and a second end, said end cap having an inlet nozzle protruding from said first end thereof, said second end of said end cap being structured to seal said first end of said first housing;

said moisture filter comprising:

a second housing having a first end and a second end;

an inlet nozzle at said first end of said second housing;

a pellet filter disposed in substantially the middle of said second housing; and an outlet nozzle extending from said second end of said second housing, said outlet nozzle of said moisture absorbing media filter communicating with said inlet nozzle of said moisture filter, wherein gas enters through said inlet nozzle of said moisture absorbing media filter, and exits through said outlet nozzle of said moisture filter.

14. The moisture absorbing media filter system of claim 13, wherein:

said opening of said moisture absorbing material becomes a tapered chamber at substantially the middle of said moisture absorbing material; and said tapered chamber having an entrance and an exit, said tapered chamber being structured to absorb more moisture at said entrance than at said exit.

15. The moisture absorbing media filter system of claim 14, wherein:

said pellet filter being separated from said moisture absorbing material by a space, said space exposing a frontal surface area of said pellet filter to the flow of gas from said tapered chamber of said moisture absorbing material, said pellet filter preventing the flow of gas when becoming substantially saturated with moisture.

16. The moisture absorbing media filter system of claim 13, further comprising:

an impermeable tube;

said end cap having a bore located at said second end thereof, said bore of said end cap communicating with said inlet nozzle of said end cap;

said impermeable tube being received by said bore of said end cap;

said end cap having a ring disposed at said second end thereof, said ring of said end cap being ultrasonically welded to said first end of said first housing; and wherein no leakage of moisture flows past the union of said ring of said end cap and said first end of said first housing, said impermeable tube fits snugly inside said bore of said end cap, wherein no gas leakage flows past the union of said impermeable tube and said bore of said end cap.

17. The moisture absorbing media filter system of claim 13 further comprising:

a dyeing agent having a color, said dyeing agent being applied to said opening in said moisture absorbing material;

said first housing being fabricated from a clear plastic, said moisture absorbing material being viewable through said clear plastic of said first housing;

said end cap being fabricated from a clear plastic, said moisture absorbing material being viewable through said clear plastic of said end cap; and said dyeing agent being applied to said moisture absorbing material, wherein said dyeing agent being forced outward through said moisture absorbing material by absorbed moisture until said dyeing agent is viewable through said first housing and said end cap, said color of said dyeing agent indicating that said moisture absorbing filter is substantially saturated with moisture.

18. The moisture absorbing media filter system of claim 17, wherein:

said first housing being fabricated from clear plastic to enable viewing propagation of said dyeing agent in said moisture absorbing material.

19. The moisture absorbing media filter system of claim 13 further comprising:

a predetermined amount of low vapor pressure, water soluble liquid being applied to said opening of said moisture absorbing filter, wherein said predetermined amount of low vapor pressure, water soluble liquid decreasing the amount of gases absorbed by said moisture absorbing material while still absorbing a sufficient amount of moisture.

20. The moisture absorbing media filter system of claim 13 further comprising:

said inlet nozzle being molded as an integral part of said second housing at said first end, said pellet filter being molded inside said second housing in substantially the middle of said second housing, said outlet nozzle being molded as an integral part of said second housing, wherein said pellet filter preventing the flow of moisture and gas through said moisture filter when said pellet filter becomes substantially saturated with moisture.

21. The moisture absorbing media filter system of claim 20, wherein:

said pellet filter having a circumferential edge and a plurality of pores; and said inlet nozzle and said outlet nozzle communicating with said circumferential edge, said pellet filter preventing the flow of dust through said moisture filter, said plurality of pores retaining the dust particles, wherein gas enters through said inlet nozzle, passes through said pellet filter and exits through said outlet nozzle.

\* \* \* \* \*